United States Patent [19]

Gredley et al.

[11] Patent Number: 4,933,511

[45] Date of Patent: Jun. 12, 1990

[54] ENANTIOSELECTIVE PREPARATION OF SUBSTITUTED 2-HYDROXYPENT-4-ENES USING OPTICALLY-ACTIVE CATALYSTS

[75] Inventors: Matthew Gredley, Parkville, Australia; Colin Wilshire, Harpenden, England

[73] Assignee: ICI Australia Limited, Melbourne, Australia

[21] Appl. No.: 35,340

[22] Filed: Apr. 7, 1987

[30] Foreign Application Priority Data

Apr. 7, 1986 [AU] Australia .................. PH5349

[51] Int. Cl.$^5$ .......................... C07C 33/42
[52] U.S. Cl. ...................... 568/845; 568/807; 568/812; 568/813; 568/823; 568/838; 568/839; 568/843; 568/849; 568/874; 568/846
[58] Field of Search ........... 568/849, 845, 879, 807, 568/812, 813, 843, 823, 838, 839, 874, 846

[56] References Cited

U.S. PATENT DOCUMENTS 3,960,973  6/1976  Staff .................... 568/849
4,117,247  9/1978  Mori et al. ............ 568/845

FOREIGN PATENT DOCUMENTS 3023488  1/1982  Fed. Rep. of Germany ...... 568/849
2131804  6/1984  United Kingdom ............ 568/845

*Primary Examiner*—Howard T. Mars
*Attorney, Agent, or Firm*—Cushman, Darby & Cushman

[57] ABSTRACT

An enantioselective process for the preparation of homoallyl alcohol enantiomer of formula II

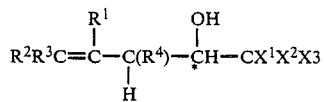

wherein:

$X^1$, $X^2$ and $X^3$ independently chosen from the group consisting of hydrogen, chlorine, bromine, fluorine, iodine, $C_1$ to $C_6$ alkyl, $C_1$ and $C_6$ haloalkyl, and haloaryl; and $R^1$, $R^2$, $R^3$ and $R^4$ are independently chosen from the group consisting of hydrogen, halogen, alkyl, alkenyl, alkynyl, benzyl, substituted benzyl, phenyl, substituted phenyl; or $R^3$ and $R^4$ is as hereinbefore defined and $R^1$ and $R^2$ form a carbocyclic or heterocyclic ring; which process comprises; reacting an aldehyde of formula III with an alkene or formula IV in the presence of an optically-active organometallic catalyst.

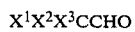

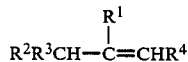

Furthermore, the compound of formula II can be isomerized to the allylic alcohol of formula I with retention of optical purity.

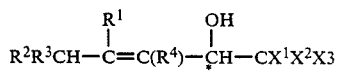

22 Claims, No Drawings

ENANTIOSELECTIVE PREPARATION OF SUBSTITUTED 2-HYDROXYPENT-4-ENES USING OPTICALLY-ACTIVE CATALYSTS

This application relates to a process for the preparation of intermediates to biologically active compounds and in particular to the stereoselective synthesis of intermediates useful in asymmetric synthesis of biologically active compounds.

It is known that in pyrethroids of general formula

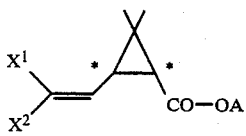

for a given alcohol moiety OA and a given pyrethroid acid moiety there is a wide variation in pesticidal activity between the two pyrethroid isomers prepared from the acid enantiomers (* indicates chiral centre).

Hatch et al (*J. Org. Chem.*, Vol 45, (1980) p. 3281) have described a convenient highly efficient synthesis of the pyrethroid acid moiety in which the stereochemistry at the two asymmetric centres is controlled by using an optically active substituted 1-halo-2-hydroxy-4-methylpent-3-ene synthetic intermediate containing a chiral C2 atom.

Optically active compositions of such 1-halo-2-hydroxy-4-methylpent-3-ene derivatives may be prepared by resolution of racemic material, however there is a need in the art for an economic stereoselective method of preparing such intermediates from readily-available materials.

We have now found that a compound of formula I with high optical purity may be prepared via its structural isomer of formula II when the isomer is formed in a stereoselective manner by condensing the appropriate aldehyde with an alkene in the presence of an optically-active organometallic catalyst.

The compound of formula II may generally be isomerised with retention of optical purity to give the compound of formula I

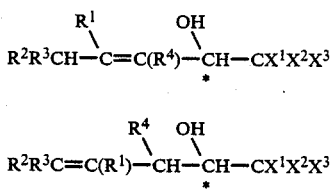

Accordingly we provide an enantioselective process for the preparation of homoallyl alcohol enantiomer of formula II

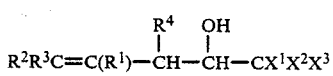

wherein:

$X^1$, $X^2$ and $X^3$ are independently chosen from the group consisting of hydrogen, halogen, $C_1$ to $C_6$ alkyl, $C_1$ to $C_6$ haloalkyl, and haloaryl; and $R^1$, $R^2$, $R^3$ and $R^4$ are independently chosen from the group consisting of hydrogen, halogen, alkyl, alkenyl, alkynyl, benzyl, substituted benzyl, phenyl, substituted phenyl; or $R^3$ and $R^4$ are as hereinbefore defined and $R^1$ and $R^2$ link to form a carbocyclic or heterocyclic ring; which process comprises reacting an aldehyde of formula III with an alkene of formula IV in the presence of an optically active organometallic catalyst.

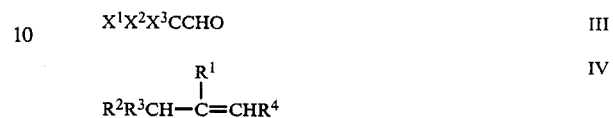

Preferably $X^1$ $X^2$ and $X^3$ are chosen from the group consisting of hydrogen, halogen methyl, trifluoromethyl and p-chlorophenyl. Most preferred $X^1$, $X^2$ and $X^3$ are bromine, chlorine and trifluoromethyl.

Generally at least one of $X^1$, $X^2$ and $X^3$ is halogen and preferably at least one is chlorine or bromine.

Preferably $R^1$, $R^2$, $R^3$ and $R^4$ are independently chosen from the group consisting of hydrogen, halogen, $C_1$ to $C_6$ alkyl, $C_1$ to $C_6$ haloalkyl, $C_1$ to $C_6$ alkenyl, $C_1$ to $C_6$ alkynyl, phenyl, benzyl, the groups benzyl and phenyl substituted with one or more substituents selected from $C_1$ to $C_6$ alkyl, halogen and $C_1$ to $C_6$ haloalkyl; or $R^1$ and $R^2$ may form a carbocyclic or heterocyclic ring of 5 to 7 constituent members and said carbocyclic ring may optionally be further substituted.

The nature of the groups $R^1$, $R^2$ and $R_3$ is not narrowly critical as the reaction with the compound of formula III will proceed efficiently with a wide variety of such groups.

It is preferred that $R^4$ is hydrogen and $R^1$, $R^2$ and $R_3$ are as hereinabove defined.

More preferably $R^1$, $R^2$, and $R^3$ are independently chosen from hydrogen, $C_1$ to $C_6$ alkyl or $R^1$ and $R^2$ form a carbocyclic ring of 5 to 7 members optionally further substituted with one or more $C_1$ to $C_6$ alkyl groups; and $R^4$ is hydrogen.

Most preferably $R^1$ is methyl and $R_2$, $R^3$ and $R^4$ are hydrogen. The product of our enantioselective process comprises a high proportion, typically 60% or more and preferably more than 75%, of one enantiomer.

Preferably the optically active organometallic reagent is chosen from said reagents in which the metal is selected from the group of titanium, aluminium, zinc, iron, tin and zirconium.

Preferably the optically-active organometallic compound is a metal complex in which the ligands are chosen from the group of halogens, alkyl groups, amines, alkoxy groups and aryloxy groups.

It is necessary that at least one ligand of the catalyst is chiral and typically at least one such ligand will be optically active and preferably is of high optical purity. Preferred examples of halogens include chlorine and bromine. Preferred examples of alkoxy/aryloxy groups include such groups derived from the group of alcohols consisting of $C_1$ to $C_6$ alkanol, 2-methyloctanol, 2,3-butanediol, menthol, quinine, cinchonine, 1,1-binaphthol and di($C_1$ to $C_6$ alkyl)esters of tartaric acid and enantiomers thereof.

Preferably ligands are chosen from the group consisting of chlorine and alkoxy/aryloxy groups derived from (S)-2-methyl-1-octanol, (2R,3R)-(−)-butanediol, (1R,2S,5R)-menthol, quinine, cinchonine, (S)-(−)-1,1'-bi-2-naphthol, (R)-(+)-1,1'-bi-2-naphthol, (1S)- endoborneol, (R)-(−)-2-octanol, (4S, 5S)-(+)-2,3-O-isopropylidene-L-threitol and (2R,3R)-diethyltartrate.

Specific examples of said optically active organometallic catalysts include [(−)-menthyloxy]titanium trichloride, [(1S)-endo-(−)-borneyloxy]titanium trichloride, di[(−)-2-octyloxy]titanium dichloride, [(−)-6′-methoxycinchonan-9-olate]titanium trichloride, [(+)-cinchonan-9-olate], [(S)-(−)-1,1′-bi-2-naphthyloxy](isopropyloxy) titanium chloride, bis[S-(−)-1,1′-bi-2-naphthyloxy]titanium, [R-(+)-1,1′-bi-2-naphthyloxy](isopropyloxy)titanium chloride, bis[R-(+)-1,1′-bis-2-naphthyloxy)titanium, [(+)-1,1′bi-2-naphthyloxy]zinc, [(S)-(−)-1,1′-bi-2-naphthyloxy]zinc, bis[(4S, 5S)-(+)2,3-O-isopropylidene-L-threitolato]titanium, bis[(2R,3R)-diethyltartrato]titanium.

Useful optically active organometallic catalysts comprising monodentate ligands are typically of formula V $$Cl_nM(OR)Y \qquad V$$

wherein OR is a monodentate ligand (which when there is more than one OR may be the same or different) derived from an alcohol or phenol, and y is an integer from 1 to 4 inclusive. At least one of the groups is generally optically active. The integer n is from 0 to 3 inclusive. The sum of y and n is 2, 3 or 4. M is chosen from zinc, aluminium, iron, zirconium and titanium.

It will be understood the total number of ligands (i.e. the sum of y and n) will depend on the nature of M and preferably the sum of y and n will be in accordance with the valency of M. For example, where M is titanium then preferably y+n is 4 and when M is zinc then preferably y+n is 2.

Typical optically active organometallic catalysts comprising at least one bidentate ligand involve complexes of formula VI

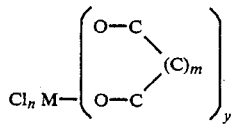

VI wherein

M is chosen from the group consisting of titanium, aluminium, tin, iron, zirconium and zinc;

y is an integer selected from the group of 1 and 2. and n is an integer selected from the group of 0 to 2 inclusive;

and in the bidendate ligand, C is a carbon which is part of a saturated or unsaturated dioxy system; and m is selected from the group of integers selected from 0 to 4 inclusive (preferably m is 0, 1 or 2).

Generally when n is 0 then y is 1 or 2; when n is 1 then y is the integer 2 and when n is 2 then y is 1.

The value 2y+n will depend on the nature of M and preferably will be in accordance with the valency of M. For example, where M is titanium, preferably 2y+n is 4.

Generally at least one of the bidentate ligands must be optically active, and when y is 2 the bidentate ligands need not be identical.

A third category of optically active organometallic catalyst comprising one bidentate ligand and at least one monodentate ligand include complexes of formula VII

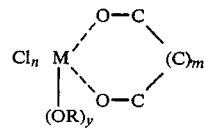

VII wherein n is an integer selected from 0 and 1;

y is an integer selected from 1 and 2 (preferably when n is 0 then y is selected from the integers 1 and 2 and when n is 1 then y is the integer 1); and M is selected from the group consisting of aluminium, iron, tin, zirconium and titanium; and the monodentate and bidentate ligands are as defined above for catalysts V and VI. Generally at least one of these ligands must be optically active.

Generally the value of the integer n+y+2 will vary depending on the nature of M and preferably will be in accordance with the valency of M. For example, when M is titanium then n+y+2 is preferably 4.

The binaphthyloxy group is an example where C is part of an unsaturated (aromatic) dioxy system and m is 2.

The conditions used in the preparation of compounds of formula II according to the present invention will depend on the nature of the reactants involved. Generally the temperature will be in the range −150° to +50° C. during the course of the reaction and preferably in the range −75° to 5° C. We have found that particularly good results are obtained when the temperature is maintained in the range −10° to 5° while combining the reactants. Reaction times will generally be in the range 0.5 hour to 100 hours and preferably 0.5 to 30 hours; however, longer or shorter reaction times and/or higher or lower temperatures may be used if desired. To reduce the incidence of unwanted side products, it is preferred in many instances to conduct the reaction under an atmosphere of an inert gas such as nitrogen or argon.

The catalyst is preferably present at a concentration in the range 0.02 to 10 mole % with respect to the aldehyde, preferably 0.2 to 10 mole % and most preferably 0.5 to 5 mole % with respect to the aldehyde. The catalyst may be recovered and reused. The process of the present invention is preferably carried out in the presence of a solvent. The nature of the solvent is not narrowly critical but preferably it is a solvent in which the catalyst and the compounds of formula III and IV are soluble. Examples of preferred solvents include solvents such as hydrocarbons, halocarbons and halocyclocarbons.

Preferred solvents include alkanes, haloalkanes and aromatic hydrocarbons.

Specific examples of compounds of formula II which may be prepared by our process include the following:

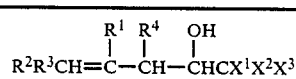

II

| | $R^1$ | $R^2$ | $R^3$ | $R^4$ | $X^1$ | $X^2$ | $X^3$ |
|---|---|---|---|---|---|---|---|
| a | $CH_3$ | H | H | H | Cl | Cl | Cl |
| b | $CH_3$ | H | H | H | Br | Br | Br |
| c | $CH_3$ | H | H | H | $CF_3$ | Cl | Cl |
| d | $CH_3$ | H | H | H | Cl | H | H |

-continued $$R^2R^3CH=\overset{R^1}{\underset{|}{C}}-\overset{R^4}{\underset{|}{CH}}-\overset{OH}{\underset{*}{CHCX^1X^2X^3}} \quad \text{II}$$

| | $R^1$ | $R^2$ | $R^3$ | $R^4$ | $X^1$ | $X^2$ | $X^3$ |
|---|---|---|---|---|---|---|---|
| e | CH$_3$ | CH$_3$ | H | H | Cl | Cl | Cl |
| f | CH$_3$ | H | H | H | Cl | Cl | –⟨○⟩–Cl |
| g | | | | | | | |

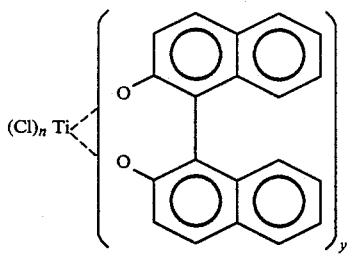

In a further aspect of the present invention we provide a catalyst which is particularly suited to the enantioselective preparation of compounds of formula II.

Accordingly we provide an organometallic catalyst of formula VIII derived from 1,1′-bi-2-naphthol

VIII wherein y is 1 and n is 2 or y is 2 and n is 0.

This is an example of the catalyst of formula VI.

Preferably the compound of formula VIII is derived from a single enantiomer of -bi-2-naphthol.

The compound of formula VIII may be prepared by reacting titanium tetrachloride with 1,1′-bi-2-naphthol. It will be understood that the degree of displacement of chloride by the bidentate ligand may be varied by control of the molar ratio and/or concentration of reactants.

Bis[1,1-bi-2-naphthyloxy)titanium may be prepared by displacement of a variety of ligands in titanium complexes. We have found it to be convenient to prepare this bis-compound by using tetra(alkoxy) titanium complexes.

Preferably the compound of formula VIII is prepared by reacting bi-2-napthol with a compound of formula Cl$_n$Ti (OR)$_q$ wherein n is equivalent to n in the desired complex of formula VIII and OR is an alkoxy group such as a C$_1$ to C$_6$ alkoxy group; and q is an integer selected from 0 and 2 and wherein q+n is 4.

We have found it to be convenient to prepare this bis-compound by reacting a tetra(alkoxy) titanium compound with an enantiomer of 1′1-bi-2-naphthol. Tetra(isopropoxy)titanium is a particularly preferred tetra(alkoxy) titanium.

Preferably the temperature is maintained in the range 0° to 150° C. during preparation of the catalyst; however, higher or lower reaction temperatures may be used if desired. Generally it is preferred to prepare the catalysts under an inert atmosphere such as may be provided using nitrogen or argon gas.

The catalyst is generally prepared in an inert solvent such as hydrocarbons, halogenated hydrocarbons. Preferred solvents are C$_1$ to C$_8$ alkanes, C$_1$ to C$_6$ haloalkanes, benzene and toluene and most preferred solvents are dichloromethane hexane and toluene.

It is preferred that the binaphthyloxy ligand is derived from (R)-(+)-1,1′-bi-2-naphthol.

As hereinbefore discussed, the compounds of formula II may be isomerised to provide allyl alcohols of formula I which are particularly useful as intermediates in asymmetric synthesis. Accordingly, in a preferred embodiment of the present invention, there is provided a process for preparation of a compound of formula I which process comprises preparing a compound of formula II by reaction of a compound of formula III with a compound of formula IV as hereinbefore described and inducing double bond migration in the resultant product of formula II to give an allyl alcohol of formula I.

Double bond migration may be induced by procedures known in the art to induce bond migration to produce an isomer favoured on thermodynamic grounds, a procedure often referred to as double bond migration, including treatment with base and treatment with acid, are given in *Advanced Organic Chemistry*, J March, pp. 533–536, McGraw Hill 2nd Ed. Treatment with acid generally results in high conversion of the compound of formula II to its allylic alcohol isomer of formula I. The temperature at which isomerization is effected is not narrowly critical. Typically the temperature is in the range −10° to +50° C. although higher or lower temperatures may be used if desired. Where bond migration is to be effected using acid the amount of acid is not narrowly critical as the acid acts as a catalyst to migration.

It is convenient to effect bond migration by mixing a solution of the compound of formula II with an acidic aqueous phase.

We have found that the compound of formula I may be prepared from its isomer of formula II with substantially complete retention of optical purity. We have also found that the catalyst for the reaction may be prepared in situ and used without further purification.

Moreover, the entire process of preparation of the compound of formula I can be carried out in a single reaction solvent without the need to isolate the catalyst or the intermediate of formula II. Furthermore the catalyst may be reused without apparent loss of activity and without adverse effects on the enantio- selectivity of the process.

These aspects make the procedure useful in large scale enantioselective preparation of compounds of formula I.

The invention is now demonstrated by, but in no way limited to, the following examples.

The solvents used were of analytical reagent grade unless otherwise stated.

EXAMPLE I

Preparation of catalyst

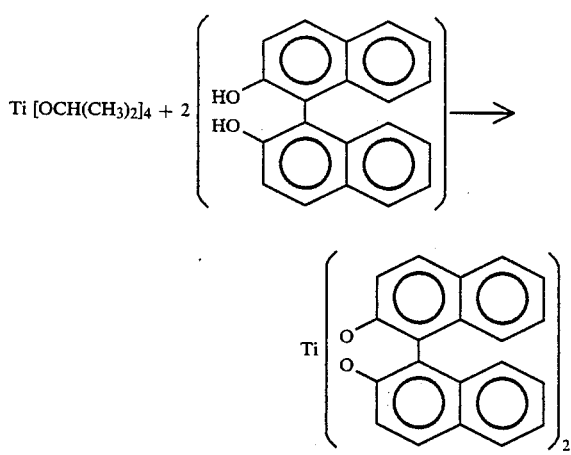

(a) To a stirred suspension of (R)-(+)-1,1'-bi-2-naphthol (455 mg, 1.59 mmole) in hexane (100 ml, dried over alumina) under an atmosphere of nitrogen, was added Ti[OCH(CH$_3$)$_2$]$_4$ (0.24 ml 0.81 mmole).

The mixture was heated to reflux and distillate (80 ml) drawn off using a Dean-Stark apparatus over 3 hours. After cooling the remaining mixture to room temperature, it was dried under vacuum to give a red solid.

(b) In a separate experiment, the procedure was repeated and the remaining mixture described above was filtered to give the solid bis [(R)-(+)-1,1'-bi-2-naphthoxy]titanium (87% yield) m.p.>280° C.;

'H n.m.r. [90 MHZ, CDCl$_3$] 7.93 (multiplet), 7.25 (multiplet); I.R.(nujol) 1620 (w), 1510 (w), 1500 (w), 1335 (w), 1240 (m) [w=weak, m=medium]

EXAMPLE 2

Preparation of 1,1,1-trichloro-2-hydroxy-4-methylpent-4-ene

To the optically-active catalyst of Example 1 (a) (total product) under nitrogen was added a solution of chloral (3.3 ml, 33.8 mmole) in dichloromethane (dried over calcium hydride) (30 ml). After cooling the solution to 0°-5° C., isobutene gas ( 2.84 g, 50 mmole) was bubbled through the mixture over about 1 min. At this stage the temperature of the mixture was not allowed to rise above 20° C. After stirring the mixture at 10°-15° C. for up to 20 h, it was poured into 10% hydrochloric acid (30 ml). After shaking the phases, the aqueous layer was separated and extracted with fresh dichloromethane (2×30 ml). The combined organic extracts were washed with water (30 ml) and dried (MgSO$_4$). Concentration of the extract gave a red oil (6.55 g, 95%) which was distilled to give the product as a colourless oil, with physical characteristics identical to those reported in the literature.

Determination of enantiomeric excess

To a stirred solution of dicyclohexylcarbodiimide (0.28 mmole) in dichloromethane (DCM) (0.17 ml) was added a solution of the alcohol (0.22 mmole) in DCM (0.19 mmole). After stirring the mixture for 5 min, a solution of either enantiomer of cyhalothrin acid (0.28 mmole) and a few crystals of 4-(N,N-dimethyl)-aminopyridine in DCM (0.65 ml) were introduced. After stirring the reaction mixture for 3 h, a portion was filtered through celite, and the filtrate analysed for product diastereomers by glc (10% FS - 1265, 4 m 200° C.), giving an ee of 43%.

EXAMPLES 3-7, 9, 10

The processes of Examples 1a and 2 were repeated with different optically-active catalysts as shown in Tables 1 and 2. The reaction time used and the resulting enantiomeric excess of the product is listed in Table 2 for different catalysts of formula V, VI or VII (wherein L is the ligand shown in the table).

EXAMPLE 8

The processes of Examples 1a and 2 were repeated with the optically active catalyst as shown in Tables 1 and 2 using the following modification: instead of using hexane, dichloromethane was used in Example 1; and then instead of drying the remaining mixture of Example 1, it was used directly in Example 2, where chloral was added to it in enough dichloromethane to bring the volume of solvent to 30 ml.

EXAMPLE 11

The process of Example 2 was repeated using the dichloromethane that had been dried over alumina rather than distilled from calcium hydride.

Preparation of Catalyst in Examples 3 to 10

Catalyst used in Examples 3 to 10 were prepared according to Example 1a except that the starting material, tetra(isopropoxy)titanium, and the alcohol, 1,1'-bi-2-naphthoxy, was replaced by starting materials and alcohols shown in Table 1 and the proportion of the alcohol was adjusted according to the desired stoichiometry.

TABLE 1

| Example | Complex | Starting Material | Alcohol | *ME |
|---|---|---|---|---|
| 3 | [(−)-menthyloxy]-titanium trichloride | Ti(OiPr)Cl$_3$ | (−)-menthol | 1 |
| 4 | [(R)-(−)-2-octyloxy]titanium trichloride | Ti(OiPr)Cl$_3$ | (R)-(−)-2-octanol | 1 |
| 5 | bis[(R)-(−)-2-octyloxy]titanium dichloride | Ti(OiPr)$_2$Cl$_2$ | R-(−)-2-octanol | 2 |
| 6 | [R-(+)-1,1'bi-2-naphthyloxy]titanium dichloride | Ti(OiPr)$_2$Cl$_2$ | R-(+)-1,1'-bi-2-naphthol | 1 |
| 7 | [(R,R)-(−)-2,3 butanedioxy]titanium dichloride | Ti(OiPr)$_2$Cl$_2$ | (R,R)-(−)-2,3-butandiol | 1 |
| 8 | [(2R,3R)-diethyl-tartrato]titanium dichloride | Ti(OiPr)$_2$Cl$_2$ | 2R,3R-diethyl-tartrate | 1 |
| 9 | [(R)-(+)-1,1'-bi-2-naphthyloxy](isopropoxy)titanium chloride | Ti(OiPr)$_3$Cl | R-(+)-1,1'-bi-2-naphthol | 1 |
| 10 | bis[(4S,5S)-(+)-2,3-isopropylidene-L-threitolate]titanium | Ti(OiPr)$_4$ | (4S,5S)-(+)-2,3-isopropylidene-L-threitol | 1 |

*Molar equivalents of alcohol based on starting material
OiPr - isopropoxy

Starting materials were prepared according to the procedure disclosed in *Spectrochimica Acta. A,* 24(8) 1213 (1968)

TABLE 2

| | | | $Cl_n Ti L_y$ V-VII | | | | |
|---|---|---|---|---|---|---|---|
| Example | n | y | Ligand (L) | | Yield | RT | EE |
| 3 | 3 | 1 | (−)-Menthyloxy | mono | 62% | 2 | 14% |
| 4 | 3 | 1 | (R)-(−)-2-octyl-oxy | mono | 71% | 4 | 10% |
| 5 | 2 | 2 | (R)-(−)-2-octyl-oxy | mono | 63% | 3–20 | 8% |
| 6 | 2 | 1 | (R)-(+)-1,1'-bi-2-naphthyl-oxy | bi | 77% | 2–19 | 18% |
| 7 | 2 | 1 | (R,R)-(−)-2,3-butanedioxy | bi | 39% | 4–19 | 24% |
| 8 | 2 | 1 | (2R,3R)-diethyl-tartrate | bi | 18% | 2.5–19 | 16% |
| 9 | 1 | 2 | isopropyloxy (R)-(+)-1,1'-bi-2-naphthyl-oxy | mono bi | 75% | 2.5–19 | 26% |
| 10 | 0 | 2 | (4S,5S)-(+)-2,3-0-isopropyli-dene-L-threitol | bi | 27% | 2.5–19 | 6% |
| 11 | 0 | 2 | (R)-(+)-1,1'-bi-2-naphthyl-oxy | bi | 95% | 20 | 48% |

RT—reaction time (hours)
EE—enantiomeric excess
mono—monodentate ligand
bi—bidentate ligand In all cases except Example 10 the same enantiomer predominated.

EXAMPLES 12–14

The process of Example 11 was repeated using the following solvents in catalyst preparation and reaction of the aldehyde and alkene. The yield and enantiomeric excess of products was recorded.

| Example | Catalyst Preparation | Reaction | Yield | EE |
|---|---|---|---|---|
| 12 | $CH_2Cl_2$ (dried over alumina) | $CH_2Cl_2$ (undried) | 95% | 48% |
| 13 | hexane | $CH_2Cl_2$ (undried) | 100% | 42% |
| 14 | hexane | toluene (sodium dried) | 83% | 48% |

EXAMPLE 15

The process of example 11 was repeated using as the reaction solvent toluene which had been dried over sodium and subsequently over activated molecular sieves. The enantiomeric excess was the same as in Example 11 and the yield of product was slightly reduced.

EXAMPLE 16

Bond Migration:

Preparation of 1,1,1-trichloro-2-hydroxy-4-methylpent-3-ene

A solution of distilled homoallyl alcohol (1.00 g, ee 43%) and toluenesulphonic acid (30 mg) in hexane (2.5 ml) was heated at 50° C. under nitrogen for 17 h. After cooling the solution, the resulting precipitate was filtered and washed with cold hexane. The filtered solid (274 mg, 29%) was pure allyl alcohol (ee 84%) The filtrate was washed with water (2×2 ml), dried ($Na_2$-$SO_4$) and evaporated to give a sticky solid (670 mg, 71%) which analysed for 19% starting material and 81% product, with a total ee +18%. The physical properties of the allylic alcohol were in agreement with those published in the literature.

Based on the enantiomeric excess of the isolated product there was no substantial loss of optical purity (no epimerisation at the chiral centre) as a result of the bond migration step.

We claim:

1. An enantioselective process for the preparation of homoallyl alcohol enantiomer of formula II

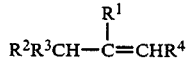

wherein:

$X^1$, $X^2$ and $X^3$ are independently chosen from the group consisting of hydrogen, halogen, $C_1$ to $C_6$ alkyl, $C_1$ to $C_6$ haloalkyl, and haloaryl; and $R^1$, $R^2$, $R^3$ and $R_4$ are independently chosen from the group consisting of hydrogen, halogen, alkyl, alkenyl, alkynyl, phenyl, benzyl, substituted phenyl or benzyl wherein the substitution is $C_1$ to $C_6$ alkyl, halogen or $C_1$ to $C_6$ haloalkyl; and wherein $R^1$ and $R^2$ may be linked to form a 5 to 7 membered carbocyclic compound; which process comprises: reacting an aldehyde of formula III with an alkene of formula IV $$X^1X^2X^3CCHO \qquad III$$

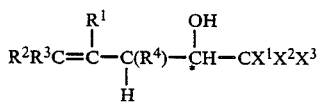

wherein $X^1$, $X^2$, $X^3$ and $R^1$, $R^2$, $R^3$ and $R^4$ are as above, in the presence of an optically active organometallic catalyst complex comprising: a metal selected from the group consisting of titanoium, aluminum, zinc, iron, tin and zirconiunm and at least one ligand which is chiral and which is selected from the group consisting of halogens, alkyl groups, amines, alkoxy groups and aryloxy groups.

2. A process according to claim 1 wherein in the compounds of formula II, III and IV, the substituents $X^1$, $X^2$ and $X^3$ are selected from the group consisting of hydrogen, chlorine, bromine, fluorine, methyl trifluoromethyl and p-chlorophenyl and at least one of $X^1$, $X^2$ and $X^3$ is selected from chlorine and bromine; $R^1$, $R^2$ and $R^3$ are independently chosen from the group consisting of hydrogen, $C_1$ to $C_6$ alkyl or wherein $R^1$ and $R^2$ are linked to form a 5 to 7 carbocyclic ring which is unsubstituted or substituted with one or more $C_1$ to $C_6$ alkyl groups; and $R^4$ is hydrogen.

3. A process according to claim 1 wherein in the compounds of formulae II, III and IV $R^1$, $R^2$, $R^3$ and $R^4$ are independently selected from hydrogen and methyl and $X^1$, $X^2$ and $X^3$ are independently selected from the group consisting of chlorine, bromine and trifluoro methyl and at least one of $X^1$, $X^2$ and $X^3$ is bromine or chlorine.

4. A process according to claim 1 wherein the product of formula II comprises at least 60% of one enantiomer.

5. A process according to claim 1 wherein the organometallic catalyst has the formula V $$Cl_nM(OR)_y \quad \quad V$$

wherein
- OR is a monodentate ligand (which when there is more than one OR may be the same or different) derived from an alcohol or phenol;
- y is an integer selected from the group consisting of 1 to 4 inclusive; and
- n is an integer selected from the group consisting of 0 to 3 inclusive; and
- M is chosen from the group consisting of zinc, aluminium, iron zirconium and titanium.

6. A process according to claim 1 wherein the organometallic catalyst has the formula VI $$Cl_n \ M \left( \begin{matrix} O-C \\ \phantom{O-}\diagdown \\ \phantom{O-C}(C)_m \\ \phantom{O-}\diagup \\ O-C \end{matrix} \right)_y \quad VI$$

wherein
- M is selected from the group consisting of titanium, aluminium, tin, iron, zirconium and zinc;
- n is an integer selected from the group of 0 to 2 inclusive;
- y is an integer selected from the group consisting of 1 and 2;
- and in the bidentate ligand C is a carbon atom which is part of a saturated or unsaturated dioxy system; and
- m is an integer selected from the group consisting of 0 to 4 inclusive.

7. A process according to claim 1 wherein the organometallic catalyst has the formula VII $$Cl_n \ M \begin{matrix} \diagup O-C \diagdown \\ \phantom{Cl_n M} (C)_m \\ | \phantom{MM} \diagdown O-C \diagup \\ (OR)_y \end{matrix} \quad VII$$

wherein;
- n is an integer selected from the groups consisting of 0 and 1;
- y is an integer selected from the group consisting of 1 and 2;
- M is selected from the group consisting of aluminium, iron, tin, zirconium and titanium;
- and in the bidentate ligand C is a carbon atom which is part of a saturated or unsaturated dioxy system; and
- m is an integer selected from the group consisting of 0 to 4 inclusive.

8. A process according to claim 1 wherein in the organometallic catalyst the metal is selected from titanium and zinc.

9. A process according to claim 1 wherein the ligands are selected from the group consisting of chlorine; bromine; and alkoxy/aryloxy groups derived from alcohols selected from the group consisting of 2-methyloctanol, 2,3-butanediol, menthol, quinine, cinchonine, 1,1'-bi-2-naphthol and enantiomers thereof; and wherein at least one of the ligands in the complex is optically active.

10. A process accordingly to claim 9 wherein the organometallic catalyst comprises at least one alkoxy/aryloxy ligand derived from alcohols selected from the group consisting of (S)-2-methyl-1-octanol, (2R, 3R)-(—)butanediol, (1R, 2S,5R)-menthol, quinine, cinchonine, (S)-(—)-1,1'-bi-2-naphthol, (R)-(+)- bi-2-naphthol, (1S)-endoborneol, (R)-(—)-2-octanol and (4S, 5S)-(+)-2,3-O-isopropylidene-L-threitol.

11. A process according to claim 1 wherein the optically active organometallic catalyst is selected from the groups consisting of:
[(—)-methyloxy]titanium trichloride,
[(11 S)-endo-(—)-borneyloxy]titanium trichloride,
di[(—)-2-octyloxy]titanium dichloride,
[(—)-6'-methoxycinchonan-9-olate]titanium trichloride,
[(+)-cinchonan-9-olate]titanium trichloride, [(S)-(—)-1,1'-bi-2-naphthyloxy](isopropyloxy)titanium chloride, bis-[R-(+)-1, 1'-bi-2-naphthyloxy](isopropyloxy)titanium chloride,
bis-[R-(+)-1,1'-bi-2-naphthyloxy]titanium,
bis-[S-(—)-1,1'-bi-2-naphthyloxy]titanium,
[R-(+)-1,1'-bi-2-naphthyloxy]zinc,
[S-(—)-1,1'bi-2-naphthyloxy]zinc,
[(2R,3R)-diethyltartrato]titanium dichloride and
[bis(42,5S)-(+)-2,3-isopropylidene-L-threitolate]titanium.

12. A process according to claim 6 wherein the organometallic catalyst is of formula VIII wherein
- y is an integer selected from 1 and 2;
- n is an integer selected from 0 and 2;
- and wherein when n is 0 then y is 2 and when n is 2 then y is 1.

13. A process according to claim 12 wherein in the catalyst of formula VIII is (1,1'-bi-2-napthoxy)titanium.

14. A process according to claim 12 wherein at least one binaphthoxy group is derived from (R)-(+)-1,1'-bi-2-naphthol.

15. A process according to claim 1 wherein the temperature is in the range —75° to 5° C.

16. A process according to claim 15 wherein the temperature is in the range —10° to 5° C.

17. A process according to claim 1 wherein the reaction is conducted under the atmosphere of an inert gas.

18. A process according to claim 1 wherein the optically active organometallic catalyst is present in the range of 0.2 to 10 mole percent with respect to the aldehyde.

19. A process according to claim 1 wherein the reaction is carried out in the presence of a solvent selected from the group consisting of alkanes, haloalkanes and aromatic hydrocarbons.

20. A process according to claim 1 which process further comprises isomerising the compound of formula II to give a compound of formula I

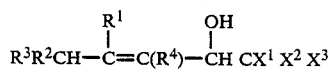
21. A process according to claim 20 wherein isomerization is effected by treating the compound of formula II with acid.
22. A process according to claim 20 wherein a solution of the compound of formula II is mixed with an acidic aqueous phase.
* * * * *